(12) United States Patent
Schwartz et al.

(10) Patent No.: US 9,396,304 B2
(45) Date of Patent: Jul. 19, 2016

(54) COMPUTER SYSTEMS FOR ANNOTATION OF SINGLE MOLECULE FRAGMENTS

(75) Inventors: David Charles Schwartz, Madison, WI (US); Jessica Severin, Cambridge (GB)

(73) Assignee: Wisconsin Alumni Research Foundation, Madison, WI (US)

( * ) Notice: Subject to any disclaimer, the term of this patent is extended or adjusted under 35 U.S.C. 154(b) by 1362 days.

(21) Appl. No.: 10/888,517

(22) Filed: Jul. 12, 2004

(65) Prior Publication Data
US 2012/0249580 A1 Oct. 4, 2012

Related U.S. Application Data

(60) Provisional application No. 60/485,725, filed on Jul. 10, 2003.

(51) Int. Cl.
| | |
|---|---|
| G01N 33/48 | (2006.01) |
| G01N 33/50 | (2006.01) |
| G06F 19/18 | (2011.01) |
| G06F 19/28 | (2011.01) |
| G09F 19/16 | (2006.01) |
| G06F 19/12 | (2011.01) |
| G06F 19/26 | (2011.01) |

(52) U.S. Cl.
CPC ............... *G06F 19/18* (2013.01); *G06F 19/12* (2013.01); *G06F 19/28* (2013.01); *G09F 19/16* (2013.01); *G06F 19/26* (2013.01)

(58) Field of Classification Search
None
See application file for complete search history.

(56) References Cited

U.S. PATENT DOCUMENTS

| | | | | |
|---|---|---|---|---|
| 5,260,203 | A * | 11/1993 | Ladner et al. | 530/387.3 |
| 5,959,458 | A * | 9/1999 | Talbot | 324/750 |
| 6,150,089 | A * | 11/2000 | Schwartz | 435/6.19 |
| 6,294,136 | B1 | 9/2001 | Schwartz | |
| 6,340,567 | B1 * | 1/2002 | Schwartz et al. | 435/6.14 |
| 6,519,583 | B1 * | 2/2003 | Koleszar et al. | 707/1 |
| 2002/0165837 | A1 * | 11/2002 | Zhang et al. | 706/16 |

OTHER PUBLICATIONS

Viani et al. Probing protein-protein interactions in real time. Nature Structural Biology, vol. 7, 2000, pp. 644-647.*
Harris. Genotator: A workbench for sequence annotation. Genome Research, 1997, vol. 7, pp. 754-762.*
Iwabuchi et al. Nucleic Acids Research, 1997, vol. 25, pp. 1662-1663.*
Schrock et al. Science, vol. 273, 1996, pp. 494-497.*
Li et al. A human muscle adenine nucleotide translocator gene has four exons, is located on chromosome 4, and is differentially expressed. The Journal of Biological Chemistry. 1989, vol. 264, pp. 13998-14004.*
Restriction fragment, 2011, 2 pages. Dorland's Illustrated Medical Dictionary. Retrieved online on Jan. 9, 2014 from <<http://www.credoreference.com>>.*
Cluster W at http://www.cbi.ac.uk/clustalw/index.html, Accessed online on Jun. 3, 2005.
Fragment Assembler at http://bio.infom-fire.it/ASSEMBLY/assemble.html, Accessed online on Jun. 3, 2005.
Zhu et al. Science, 293(5537):2101-05, 2001, Global analysis of protein activities using protecme chips.
The International Ergonomics Association at http://www.iea.cc, Accessed online on Jun. 3, 2005.
MySQL at http://www.mysql.com/, Accessed online on Jun. 3, 2005.
GTK Library at http://www.gtk.org/, Accessed online on Jun. 3, 2005.
Lai et al., Nature Genetics, 23:309-313, 1999.

* cited by examiner

*Primary Examiner* — Russell S Negin
(74) *Attorney, Agent, or Firm* — Quarles & Brady, LLP

(57) ABSTRACT

There are provided computer systems for visualizing and annotating single molecule images. Annotation systems in accordance with this disclosure allow a user to mark and annotate single molecules of interest and their restriction enzyme cut sites thereby determining the restriction fragments of single nucleic acid molecules. The markings and annotations may be automatically generated by the system in certain embodiments and they may be overlaid translucently onto the single molecule images. An image caching system may be implemented in the computer annotation systems to reduce image processing time. The annotation systems include one or more connectors connecting to one or more databases capable of storing single molecule data as well as other biomedical data. Such diverse array of data can be retrieved and used to validate the markings and annotations. The annotation systems may be implemented and deployed over a computer network. They may be ergonomically optimized to facilitate user interactions.

13 Claims, 3 Drawing Sheets

COMPUTER SYSTEMS FOR ANNOTATION OF SINGLE MOLECULE FRAGMENTS

The work described herein in this disclosure was conducted with United States government support awarded by the Department of Energy, number DE-FG02-99ER62830. The United States has certain rights in the invention(s) of this disclosure.

REFERENCE TO A COMPUTER PROGRAM LISTING APPENDIX

A computer program listing appendix has been submitted via EFS-Web and is incorporated by reference herein in its entirety. The computer program listing appendix is contained in a file entitled "960296-00604.txt," which is 90,409 bytes and was created on Jun. 13, 2016.

FIELD

The present disclosure relates in general to visualization and processing of single molecule images. Specifically, embodiments of the present disclosure provide computer systems that enable a user to visualize and annotate molecules and fragments in the single molecule images for further Processing. Embodiments according to this disclosure provide access to one or more databases containing a diverse array of biomedical information in addition to the single molecule data, thereby allowing a user to validate the marking and annotations. Embodiments described herein are thus useful in studies of any macromolecules such as DNA, RNA, and proteins.

BACKGROUND

Modern biology, particularly molecular biology, has focused itself in large part on understanding the structure, function, and interactions of essential macromolecules in living organisms such as nucleic acids and proteins. For decades, researchers have developed effective techniques, experimental protocols, and in vitro, in vivo, or in situ models to study these molecules. Knowledge has been accumulating relating to the physical and chemical traits of proteins and nucleic acids, their primary, secondary, and tertiary structures, their roles in various biochemical reactions or metabolic and regulatory pathways, the antagonistic or synergistic interactions among them, and the on and off controls as well as up and down regulations placed upon them in the intercellular environment. The advance in new technologies and the emergence of interdisciplinary sciences in recent years offer new approaches and additional tools for researchers to uncover unknowns in the mechanisms of nucleic acid and protein functions.

The evolving fields of genomics and proteomics are only two examples of such new fields that provide insight into the studies of biomolecules such as DNA, RNA, and protein. New technology platforms such as DNA microarrays and protein chips and new modeling paradigms such as computer simulations also promise to be effective in elucidating protein, DNA and RNA characteristics and functions. Single molecule optical mapping is another such effective approach for close and direct analysis of single molecules. See, U.S. Pat. No. 6,294,136, the disclosure of which is fully incorporated herein by reference. The data generated from these studies—e.g., by manipulating and observing single molecules—constitutes single molecule data. The single molecule data thus comprise, among other things, single molecule images, physical characteristics such as the length, shape and sequence, and restriction maps of single molecules. Single molecule data provide new insights into the structure and function of genomes and their constitutive functional units.

Images of single molecules represent a primary part of single molecule datasets. These images are rich with information regarding the identity and structure of biological matter at the single molecule level. It is however a challenge to devise practical ways to extract meaningful data from large datasets of molecular images. Bulk samples have conventionally been analyzed by simple averaging, dispensing with rigorous statistical analysis. However, proper statistical analysis, necessary for the accurate assessment of physical, chemical and biochemical quantities, requires larger datasets, and it has remained intrinsically difficult to generate these datasets in single molecule studies due to image analysis and file management issues. To fully benefit from the usefulness of the single molecule data in studying nucleic acids and proteins, it is essential to meaningfully process these images and derive quality image data.

Effective methods and systems are thus needed to accurately extract information from molecules and their structures using image data. For example, a large number of images may be acquired in the course of a typical optical mapping experiment. To extract useful knowledge from these images, effective systems are needed for researchers to evaluate the images, to characterize DNA molecules of interest, and to assemble, where appropriate, the selected fragments thereby generating longer fragments or intact DNA molecules. This is particularly relevant in the context of building genome-wide maps by optical mapping, as demonstrated with the ~25 Mb *P. falciparum* genome (Lai et al, *Nature Genetics* 23:309-313, 1999).

The *P. falciparum* DNA, consisting of 14 chromosomes ranging in size from 0.6-3.5 Mb, was treated with either NheI or BamHI and mounted on optical mapping surfaces. Lambda bacteriophage DNA was co-mounted and digested in parallel to serve as a sizing standard and to estimate enzyme cutting efficiencies. Images of molecules were collected and restriction fragments marked, and maps of fragments were assembled or "contiged" into a map of the entire genome. Using NheI, 944 molecules were mapped with the average molecule length of 588 Mb, corresponding to 23-fold coverage; 1116 molecules were mapped using BamHI with the average molecule length of 666 Mb, corresponding to 31-fold coverage (Id at FIG. 3). Thus, each single-enzyme optical map was derived from many overlapping fragments from single molecules. Data were assembled into 14 contigs, each one corresponding to a chromosome; the chromosomes were tentatively numbered 1, the smallest, through 14, the largest.

Various strategies were applied to determine the chromosome identity of each contig. Restriction maps of chromosomes 2 and 3 were generated in silico and compared to the optical map; the remaining chromosomes lacked significant sequence information. Chromosomes 1, 4 and 14 were identified based on size. Pulsed field gel-purified chromosomes were used as a substrate for optical mapping, and their maps aligned with a specific contig in the consensus map. Finally, for some chromosomes, chromosome-specific YAC clones were used. The resulting maps were aligned with specific contigs in the consensus map (Id at FIG. 4). Thus, in this experiment multi-enzyme maps were generated by first constructing single enzyme maps which were then oriented and linked with one another. Such maps may be linked together by a series of double digestions, by the use of available sequence information, by mapping of YACs which are located at one end of the chromosome, or by Southern blotting.

In short, optical mapping is powerful tool used to construct genome-wide maps. The data generated as such by optical mapping may be used subsequently in other analyses related to the molecules of interest, for example, the construction of restriction maps and the validation of DNA sequence data. There is accordingly a need for systems for visualizing, annotating, aligning and assembling single molecule fragments. Such systems should enable a user to effectively process single molecule images thereby generating useful single molecule data; such systems should also enable the user to validate the resulting data in light of the established knowledge related to molecules of interest. Robustness in handling large image datasets is desired, as is rapid user response.

SUMMARY

It is therefore an object of this disclosure to provide computer systems for visualizing and annotating single molecule images. Particularly, in the case of nucleic acid molecules, embodiments of the annotation system described herein allow a user to annotate single molecules of interest and their restriction enzyme cut sites, thereby determining the restriction fragments of single molecules. One or more connectors are included in the annotation system which connect to one or more databases capable of storing single molecule data as well as other biomedical data. Such diverse array of data can be retrieved and used to validate the markings and annotations. In certain embodiments, the annotations and markings may be automatically generated by the system based on the relevant information input by the user or available in the connected database. In alternative embodiments, the markings and annotations may be manually added to the images by a user through the user interface. The annotation systems may be implemented and deployed over a computer network. They may be ergonomically optimized to facilitate user interactions.

In accordance with this disclosure, there is provided, in one embodiment, a computer system for annotating single molecule images, wherein the single molecule images comprise signals derived from individual molecules or individual molecular assemblies or polymers, which system comprises: a connector connecting to a database comprising data from single molecule images; and a user interface capable of displaying said single molecule images and markings or annotations on said single molecule images.

According to one embodiment, the user interface allows a user to mark up and thereby annotate the single molecule images.

According to another embodiment, the signals are optical, atomic, or electronic. According to another embodiment, the signals are generated by atomic force microscopy, scan tunneling microscopy, flow cytometry, optical mapping, or near field microscopy.

According to another embodiment, the single molecule images are derived from optical mapping of single molecules, the single molecules are individual molecules or individual molecular assemblies or polymers. According to yet another embodiment, the single molecules are selected from the group consisting of (i) nucleic acid molecules and (ii) protein or peptide molecules.

According to another embodiment, the database comprises single molecule data, wherein the single molecule data comprises one or more single molecule images. According to yet another embodiment, the single molecule data further comprises one or more restriction maps. According to a further embodiment, the single molecule data further comprises one or more sequences. According to a still further embodiment, the sequences are nucleotide sequences or amino acid sequences.

According to another embodiment, the database is further capable of storing other biomedical data, wherein the other biomedical data is derived from one or more biomedical technology platforms.

According to another embodiment, the database comprises one or more data files. According to yet another embodiment, the database is a relational database. According to still another embodiment, the database is an object database.

According to another embodiment, the single molecule annotation system further comprises one or more additional connectors, each connecting to an additional database. According to yet another embodiment, the additional database is capable of storing single molecule data. In another embodiment, the single molecule data comprises one or more single molecule images. In yet another embodiment, the single molecule data further comprises one or more restriction maps. In still another embodiment, the single molecule data further comprises one or more sequences. In a further embodiment, the sequences are nucleotide sequences or amino acid sequences. According to a still further embodiment, the additional database is capable of storing other biomedical data, wherein the other biomedical data is derived from one or more biomedical technology platforms.

According to another embodiment, the single molecule annotation system is implemented and deployed over a computer network.

According to another embodiment, the markings or annotations (i) identify single molecules of interest and (ii) identify restriction enzyme cut sites thereby delineating the restriction fragments of single molecules, which single molecules are nucleic acid molecules. According to yet another embodiment, the markings and annotations are overlaid translucently onto the single molecule images. According to still another embodiment, the annotation system further allows a user to ergonomically mark up and annotate single molecule images through the user interface.

According to another embodiment, the computer system further comprises an image caching system capable of reducing image processing time, wherein the image processing comprises (i) displaying single molecule images and (ii) marking and annotating the single molecule images. According to yet another embodiment, the image caching system ensures that the single molecule image data is accessed on a load-on-demand basis. According to still another embodiment, the image caching system comprises a tile cache supporting display of tiles of images, which tiles are of a predetermined size.

DETAILED DESCRIPTION

Brief Discussion of Relevant Terms

Figure 1:
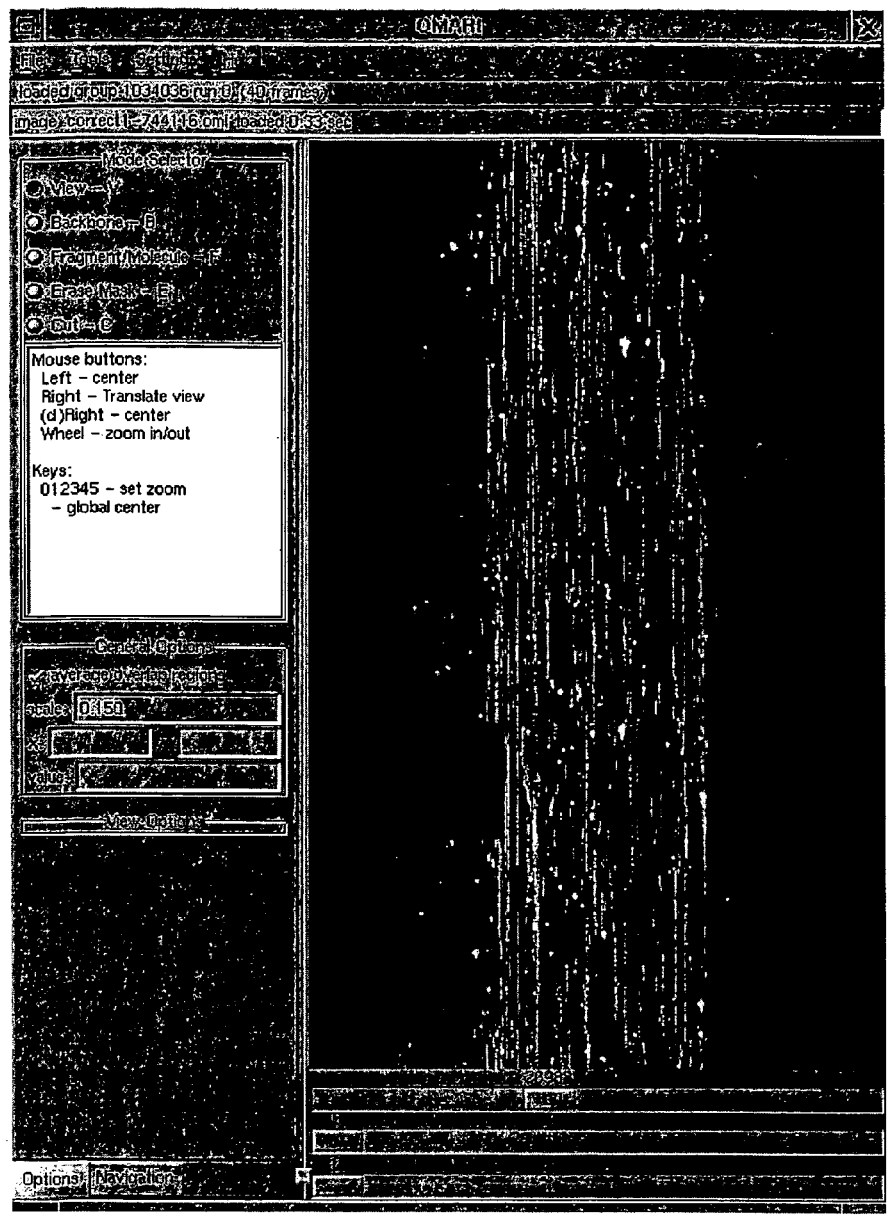
FIG. 1 is a screenshot of the user interface of the computer system for annotating single molecule images according to one embodiment of this disclosure, showing a plurality of single DNA molecule fragments.

The following disciplines, molecular biology, microbiology, immunology, virology, pharmaceutical chemistry, medicine, histology, anatomy, pathology, genetics, ecology, computer sciences, statistics, mathematics, chemistry, physics, material sciences and artificial intelligence, are to be understood consistently with their typical meanings established in the relevant art.

As used herein, genomics refers to studies of nucleic acid sequences and applications of such studies in biology and medicine; proteomics refers to studies of protein sequences, conformation, structure, protein physical and chemical properties, and applications of such studies in biology and medicine.

The following terms: proteins, nucleic acids, DNA, RNA, genes, macromolecules, restriction enzymes, restriction maps, physical mapping, optical mapping, optical maps (restriction maps derived from optical mapping), hybridization, sequencing, sequence homology, expressed sequence tags (ESTs), single nucleotide polymorphism (SNP), CpG islands, GC content, chromosome banding, and clustering, are to be understood consistently with their commonly accepted meaning in the relevant art, i.e., the art of molecular biology, genomics, and proteomics.

The following terms, atomic force microscopy (AFM), scan tunneling microscopy (STM), flow cytometry, optical mapping, and near field microscopy, etc., are to be understood consistently with their commonly accepted meanings in the relevant art, i.e., the art of physics, biology, material sciences, and surface sciences.

The following terms, database, database server, data warehouse, operating system, application program interface (API), programming languages, C, C++, Extensible Markup Language (XML), SQL, as used herein, are to be understood consistently with their commonly accepted meanings in the relevant art, i.e., the art of computer sciences and information management. Specifically, a database in various embodiments of this disclosure may be flat data files and/or structured database management systems such as relational databases and object databases. Such a database thus may comprise simple textual, tabular data included in flat files as well as complex data structures stored in comprehensive database systems. Single molecule data may be represented both in flat data files and as complex data structures.

As used herein, single molecules refer to any individual molecules, such as macromolecule nucleic acids and proteins. A single molecule according to this disclosure may be an individual molecule or individual molecular assembly or polymer. That is, for example, a single peptide molecule comprises many individual amino acids. Thus, the terms "single molecule," "individual molecule," "individual molecular assembly," and "individual molecular polymer" are used interchangeably in various embodiments of this disclosure. Single molecule data refers to any data about or relevant to single molecules or individual molecules. Such data may be derived from studying single molecules using a variety of technology platforms, e.g., flow cytometry and optical mapping. The single molecule data thus may comprise, among other things, single molecule images, physical characteristics such as lengths, heights, dimensionalities, charge densities, conductivity, capacitance, resistance of single molecules, sequences of single molecules, structures of single molecules, and restriction maps of single molecules. Single molecule images according to various embodiments comprise signals derived from single molecules, individual molecules, or individual molecule assemblies and polymers; such signals may be optical, atomic, or electronic, among other things. For example, a single molecule image may be generated by, inter alia, atomic force microscopy (AFM), flow cytometry, optical mapping, and near field microscopy. Thus, electronic, optical, and atomic probes may be used in producing single molecule images according to various embodiments. In certain embodiments, various wavelengths may be employed when light microscopy is used to generate single molecule images, including, e.g., laser, UV, near, mid, and far infrared. In other embodiments, various fluorophores may be employed when fluorescent signals are acquired. Further, single molecule images according to various embodiments of this disclosure may be multi-spectral and multi-dimensional (e.g., one, two, three-dimensional).

As used herein, genomics and proteomics data refers to any data generated in genomics and proteomics studies from different technology platforms; and biomedical data refers to data derived from any one or more biomedical technology platforms.

As used herein, the term "contig" refers to a nucleotide (e.g., DNA) whose sequence is derived by clustering and assembling a collection of smaller nucleotide (e.g., DNA) sequences that share certain level of sequence homology. Typically, one manages to obtain a full-length DNA sequence by building longer and longer contigs from known sequences of smaller DNA (or RNA) fragments (such as expressed sequence tags, ESTs) by performing clustering and assembly.

As used herein, the term "single molecule assembly" refers to larger single molecule fragments assembled from smaller fragments. In the context of nucleic acid single molecules, "assembly" and "contig" are used interchangeably in this disclosure.

The term "array" or "microarray" refers to nucleotide or protein arrays; "array," "slide," and "chip" are interchangeable where used in this disclosure. Various kinds of nucleotide arrays are made in research and manufacturing facilities worldwide, some of which are available commercially. (e.g., GeneChip™ by Affymetrix, Inc., LifeArray™ by Incyte Genomics). Protein chips are also widely used. See Zhu et al., *Science* 293(5537):2101-05, 2001.

A user interface, or a viewer, as used herein and interchangeably, refers to any kind of computer-application or program that enables interactions with a user. A user interface or viewer may be a graphical user interface (GUI), such as a browser. Examples of such a browser include Microsoft Internet Explorer™ and Netscape Navigator™. A user interface also may be a simple command line interface in alternative embodiments. A user interface of the invention(s) of this disclosure may also include plug-in tools that extend the existing applications and support interaction with standard desktop applications. A user interface in certain embodiments of the invention(s) of this disclosure may be designed to best support users' browsing activities according to ergonomic principles.

"Ergonomically optimized," as used herein, refers to optimization on the design and implementation of the assembly system based on ergonomics principles. The International Ergonomics Association defines ergonomics as both the scientific discipline "concerned with the understanding of interactions among humans and other elements of a system," as well as the profession "that applies theory, principles, data and methods to design in order to optimize human well-being and overall system performance." "Ergonomists contribute to the design and evaluation of tasks, jobs, products, environments and systems to make them compatible with the needs, abilities and limitations of people." Ergonomically optimized systems according to this disclosure provide reduced error rate and improved efficiency and quality in user interaction.

Computer Annotation System: Single Molecule Visualization and Annotation

The computer annotation system according to this disclosure features a user-friendly interface capable of displaying and annotating single molecule images for further processing. It also features a connector that connects to a database having stored therein single molecule images. Such a database may be a flat file, a relational database, an object database or a data warehouse in various embodiments according to this disclosure. The single molecule images can thus be loaded from a flat file or a relational database such as MySQL, for example, and displayed and annotated through the user interface. The marking or annotation process involves the identification of molecules of interest and the identification of restriction enzymes cut sites which, in turn, identify the restriction fragments. The process also involves the identification of problematic regions such as overlapping or tangled DNA molecules or fragments in certain embodiments. The end result of the marking and annotation process is therefore that each restriction fragment recognized in image view as having acceptable clarity and image resolution is identified and masked.

An additional characteristic of the computer annotation system in certain embodiments is an ergonomically optimized GUI (Graphical User Interface). Established ergonomic principles as discussed supra are adopted. Human-assisted image data mark-up functionality was improved upon from an existing system and implemented in the present annotation system to enhance user efficiency and productivity. Several analyses were performed to guide its development. These included an analysis of user techniques with the former annotation programs, and the addition of ergonomic analysis techniques of reduced motion, most common usage, clever use of functionality clustering and mode overloading.

Many individuals are required to process (i.e., examine and mark-up) the large volume of image data in the annotation system. Because of the often brief and primarily transient nature of hourly student help in a university laboratory setting, required features of the annotation system included the speed and ease with which a it could be learned and applied. The computer annotation system in various embodiments according to this disclosure allows an ease of flow from one task to the next using minimal wasted movement or time, and a short user learning curve. Several examination and mark-up activities are grouped into five work modes (view, backbone, fragment, cut, and erase) with the short cut keys "v," "b," "f," "c" and "e," respectfully. These modes include viewing groups of images, marking individual fragments within a single molecule for saving as data sets and manually adding "missing cuts" and "erasing" extraneous noise in close proximity to selected molecules. The short cut keys are clustered in a standard QWERTY keyboard around the left-hand anchor position. Full utilization of all three mouse buttons and the mouse wheel also contribute to the annotation system's effectiveness. The most common activities, always available to the user regardless of mode are panning and zooming. At all times the right mouse button implements a click-drag interface to panning the super-image. Zooming is accomplished through two different interfaces which are described further below.

FIG. 1 is a screenshot of the user interface for the computer annotation system according to one embodiment of this disclosure. In the window to the right of the screen is displayed a collage of images of single DNA molecules or single DNA molecule fragments. These images are derived from optical mapping of single DNA molecules. Across the top left, just beneath the menu bar (File, Tools, Settings and Help) which can be customized, is the group identification and frame numbers and the process or "run" that has generated them. Information displayed here can also be customized. This image-related information is stored and retrieved from the database connected to the computer annotation system as the images are loaded to the system and displayed for viewing by the user.

On the left of the image display window, are several radio buttons showing different modes in which the system can be operated. The view mode in the annotation system provides the user with a bird's eye view of the group of images to examine the molecules and fragments within a channel (thin region on the slide), while the image frames—the outlines of each successive image along a channel—may be superimposed on it. Because a group of images can be shown in a single screen the user can easily follow a molecule as it spans the length of several images. This is an improvement over an earlier system in which only individual images could be viewed at a time, making it more difficult to mentally connect continuing portions of the same molecule(s) through successive frames. The user enters view mode in the annotation system by depressing the "v" key or selecting from the options on the left-hand side bar (FIG. 1). In view mode the user can select and highlight one or more molecules for further processing. Visible within each group of images in a single channel is a mix of large "genomic molecules", as well as smaller "standards" or "standard molecules" which represent fragments of known sequence of plasmid. Additional smaller pieces of cleaved genomic DNA or other fluorescent contamination may also be visible in a channel and must be ignored. View mode allows a group of images to be viewed at several levels of magnification using the zoom feature. One of the easiest and most rapid methods of changing the magnification of the image(s) on the screen is by rolling the center wheel on the mouse. The magnification of the group of images comprising a channel can also be specified numerically on the left-hand panel to any number greater than 0.0 and less then or equal to 8.0. The number keys 1, 2, 3 and 4 and the "~" key (just left of the number 1 key) are pre-coded allowing an ease to shifting between levels of magnification or compression for viewing the images as follows:

1=1:1, no magnification or compression;

2=1:2, 1 pixel in the original image is 2 pixels on the screen;

3=1:3, 1 pixel in the original image is 3 pixels on the screen;

4=1:4, 1 pixel in the original image is 4 pixels on the screen; and

"~" key=5:1, 5 pixels in the original image are compressed to 1 pixel on the screen.

A click-drag panning feature allows the user to move around in the window examining different portions of the same group of images—with or without the image frames shown—at any of the available levels of magnification. This is also an improvement from the former system which used scrollbars on the bottom and side of the images to enable viewing of an image not visible entirely within the window. Although primarily used as a development tool another important feature in view inode is that the user can, by positioning the cursor over a location in a molecule and left-clicking on it, view both the XY coordinates of that point as well as the raw data intensity of the point (after flattening the image). Successive clicks will also measure distances in data pixels to allow a user a means of sizing parts of the image.

Using the annotation system, "manual" or "backbone" mark-up are the two methods used to prepare data for map generation. Regardless of which is chosen, the goal is to define a molecule of interest within a channel for mapping. Manual mark-up, described further below, involves use of the "fragment", "cut" and "erase" modes, each of which is entered from the side bar options or by pressing the "f", "c" or e" keys, respectively. Backbone mark-up involves the user defining a line superimposed over the image of the DNA molecule of interest in the channel. Backbone mode is designed to guide the subsequent fragment mark-up, cut identification and extraneous material erasing functionality by identifying the molecule(s) of interest from background noise and by defining a path of their location(s). A series of highlighted fragments can thus form a backbone of a single molecule. The assessment of subsequent fragments may then be performed in reference to this backbone.

The user depresses the "b" key to enter the "backbone" mark-up mode, locates the molecule of interest, then left-clicks the mouse to define a starting inflection point at one end of a fragment and an end inflection point, either at the obvious end of the molecule or some other chosen location along the molecule. The program draws a straight line connecting these points, providing the appearance of a line superimposed on the DNA image. The user can also build off the end of a line by clicking from the end point to some point in "space." The user can also click on and drag the line at any location in between the start/end points add additional inflection points following the general line of the molecule more closely. Alternatively, several points may be chosen in succession as the user closely follows the molecule from one end to the other (or to some other end point in the molecule) along the channel. The superimposed line should accurately follow the molecule but need not be precisely drawn, since there is a margin of about 10 pixels flanking the width of the imaged molecule in which the superimposed line may lie and still capture the molecule of interest. Inflection points defining the line may also be deleted by clicking to select an inflection point and depressing the delete key. The use of backbone mark-up mode most often requires at least some amount of manual mark-up alteration (see below) after further processing of the data. Following completion of any modifications, the data are stored in a file associated with the group/channel and later exported for final map making. In Example 1 infra, an object "MoleculeBackbone" is implemented as a C++ class which represents the mark-up information of single molecules in the computer annotation system in accordance with one embodiment of this disclosure.

"Manual" mark-up technique alone also produces data that are exported for final map making, but in contrast to the semi-automated backbone mark-up mode, manual mark-up allows the user complete control over selection of fragments, cuts and inclusion or exclusion of signal. When performing manual mark-up, the user employs the individual "fragment," "cut" and "erase" modes of the annotation system within various embodiments according to this disclosure. Specifically, manual mark-up involves the user manually identifying individual fragments and restriction sites (cuts) along a genomic molecule as well as manually, adding cuts where they likely should have been identified by the program but were missed. Finally, the user may also "erase" miscellaneous signal (noise) in the image that might otherwise be confused with true genomic DNA signal.

The data files imported to the annotation system following initial image collection include threshold intensity levels for each image calculated during the flattening process. The annotation system averages these intensity values for a single, moderate threshold intensity level for the group of images; manual mark-up mode in the annotation system uses this value to discern what intensity levels are background (below threshold) versus the DNA image (above threshold, in blue tint). Although the threshold average is pre-calculated by the preceding process, the user has the ability, after entering "fragment" mode (using the "f" key) to adjust, i.e., reduce but not eliminate, the dimly lighted area or "bloom" surrounding each fragment. Some of the bloom may represent glow from light scattering from the microscope optics or an artifact from the CCD camera, but at least a portion of it likely represents real data that if omitted at this step would affect fragment sizing. Setting the threshold value is in fact a trial and error process if the user determines that a change from the pre-calculated value is necessary. If altered by the user, the threshold value should not be altered again once manual mark-up has begun. After a threshold has been decided upon, the blue threshold tint can be disabled to provide a clearer view of the images.

Briefly, once the user chooses a molecule in the channel and determines that the threshold level is appropriate for the data, the user places the cursor anywhere above the first fragment in the molecule and left-clicks to select it. The color of the fragment will change to a translucent pale purple; the user continues to select successive fragments one by one, each of which when selected will turn translucent purple, As the next is selected, the former will change to either a translucent pale yellow or translucent turquoise color. The previously selected fragments alternate in this yellow/turquoise scheme, allowing the user to visualize where fragments begin and end as well as to identify fragments that might require cutting, further described below. If the user returns to select any of the previously selected fragments, the fragment color returns to translucent purple and the colors of each of the other fragments within that molecule alternate in colors of turquoise and pale yellow. A fragment can also be deleted from the selected group of fragments in the molecule by first selecting it, then depressing the "delete" key. When the user has completed the fragment identification/selection process for a molecule, the user then "exits" the molecule by center-clicking on the rolling wheel of the mouse, and the colors of each of the fragments within that molecule change to translucent green. To mark-up a different molecule in the channel one must first exit the currently active molecule.

Figure 2:
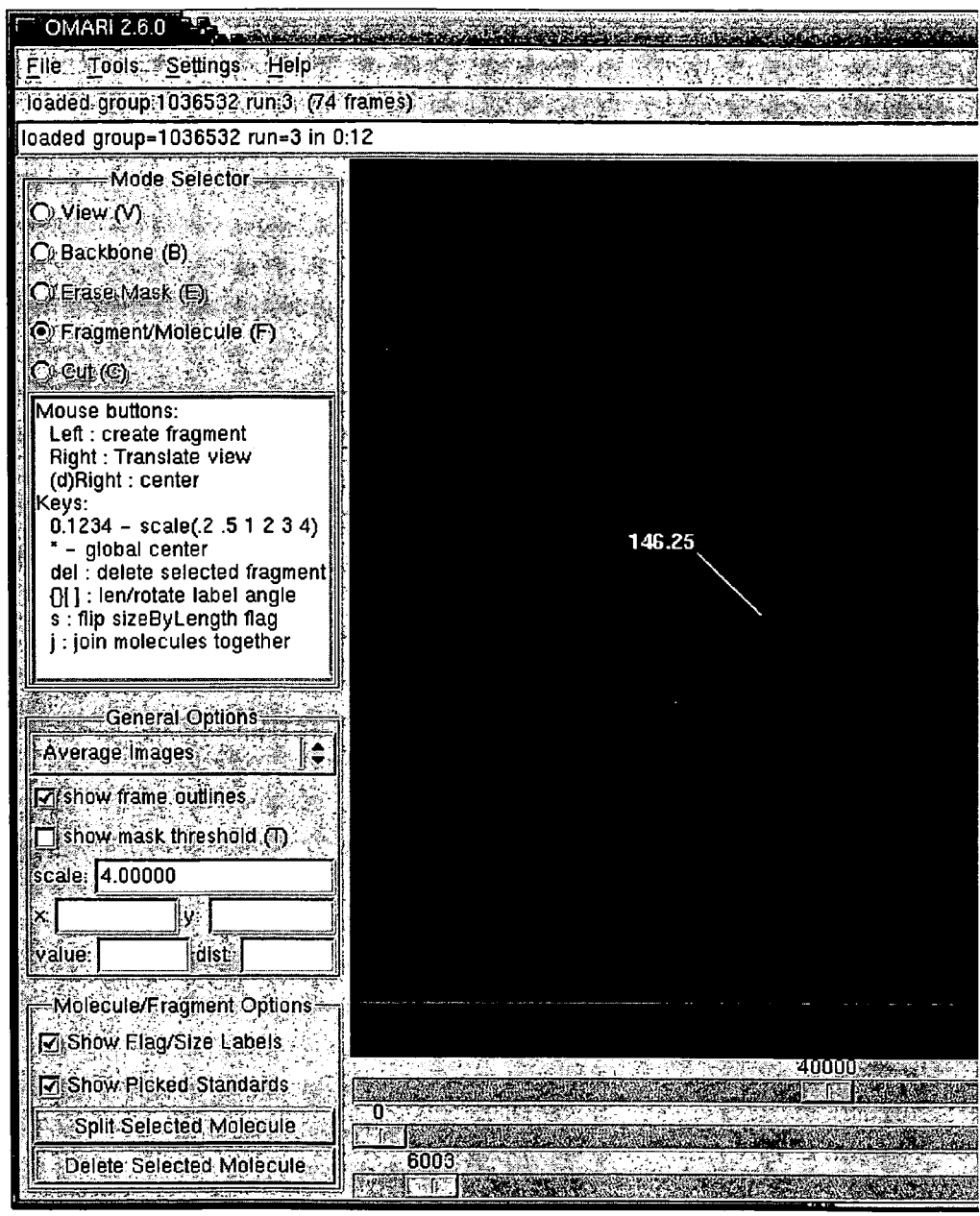
FIG. 2 is a screenshot of the user interface of the computer system for annotating single molecule images according to another embodiment of this disclosure, showing one marked-up single molecule fragment.

FIG. 2 shows, in fragment mode, a single molecule fragment with its length denoted by the number displayed in the image window. Similarly, FIG. 3 in fragment mode shows a series of marked fragments belonging to a single molecule. These fragments are thus designated as selected restriction fragments, and may be used for subsequent analyses, e.g., construction of restriction maps.

If a section of "messy" DNA, clearly part of which belongs to the continuing molecule, interrupts the selection of fragments, the user may exit the existing molecule, skip over the messy DNA, begin selecting fragments in the obviously continuing molecule, then link the two portions to signify that they belong together in the same molecule. These sections of molecule are linked in the following manner: While the second portion of the molecule is still "active" (has not been exited as the first has), the user places the cursor over the inactive first portion of the molecule. Without clicking on it, the user depresses the "j" key to join (link but not physically connect on-screen) the two sections of the molecule. The user can then return to the messy DNA and clean it up by placing (obviously missing) cuts, if necessary, and "erasing" any signal from miscellaneous DNA that may overlap the true signal. To add cuts, the user enters the "cut" mode (by depressing the "c" key) and positions the cursor in an area that appears to the user as though a cut should have been made at that location but was not. The angle at which the cut is made must also be specified and is easily accomplished by rolling the middle wheel of the mouse to the appropriate rotation for the cursor, then left-clicking to set the cut. The cut appears as a small red line and the fragment is cut and tinted with alternating colors of pale turquoise and yellow to clearly denote the existence of now two separate fragments. Users are trained to recognize where a cut was likely missed. Adding too many cuts where they should not be placed introduces errors that are often not resolvable and may result in the map being unusable in the assembly process. If a cut is added and later it is determined to have been made in error, the cut can be removed and the fragment rejoined by moving the cursor while in cut mode above the location of a misplaced cut, noticing a box outline form around the cut, and depressing the delete key.

The "erase" mode, entered by depressing the "e" key or selecting from the options on the left of the image window, allows the user to erase or paint over portions of the image in close proximity to the molecule to eliminate artifact signal that would otherwise interfere with subsequent processing. If the messy DNA fragment in the image discussed above were the result of imaging together two or more fragments, portions of which may be overlapping, the contribution of the intensity of an overlapping fragment could be, in large part, painted out or erased from areas surrounding the image of the DNA molecule selected for processing. However, since an area of direct overlap could not be erased in this fragment and would be detected as having (albeit falsely) high intensity for the molecule of interest, the fragment could be flagged, directing it for later special processing. To accomplish this, the user must first return to fragment mode and highlight the fragment by left-clicking on it; then depress the "s" key for "sizing." An "F" will appear next to a line drawn to the flagged fragment. Once the fragment is labeled in this manner, during subsequent processing the length-related data for the fragment will be more heavily weighted than its overall intensity.

The techniques used in the "erase" mode of the annotation system are typical paint program features. The options in this mode relate to the "thickness" of the brush used to paint, an unerase feature accomplished by a click-and-drag technique with the middle mouse button, and an "erase over" feature, which allows one to start with a messy fragment and simultaneously add erase mask and remove fragment mask from the fragment.

Thus, in certain embodiments according to this disclosure the molecule mark up and image visualization in the computer annotation system may be implemented as translucent overlays. See, e.g., Example 3 infra for the rendering of colored mark ups. Such translucent overlays allow the user to view all features of single molecule images even after the mark up is completed and thereby facilitate the user's evaluation and analysis concerning the selected molecules. That is, the user would not need to switch between viewing and hiding the mark up as what he or she would have to in the absence of translucent overlays.

Figure 3:
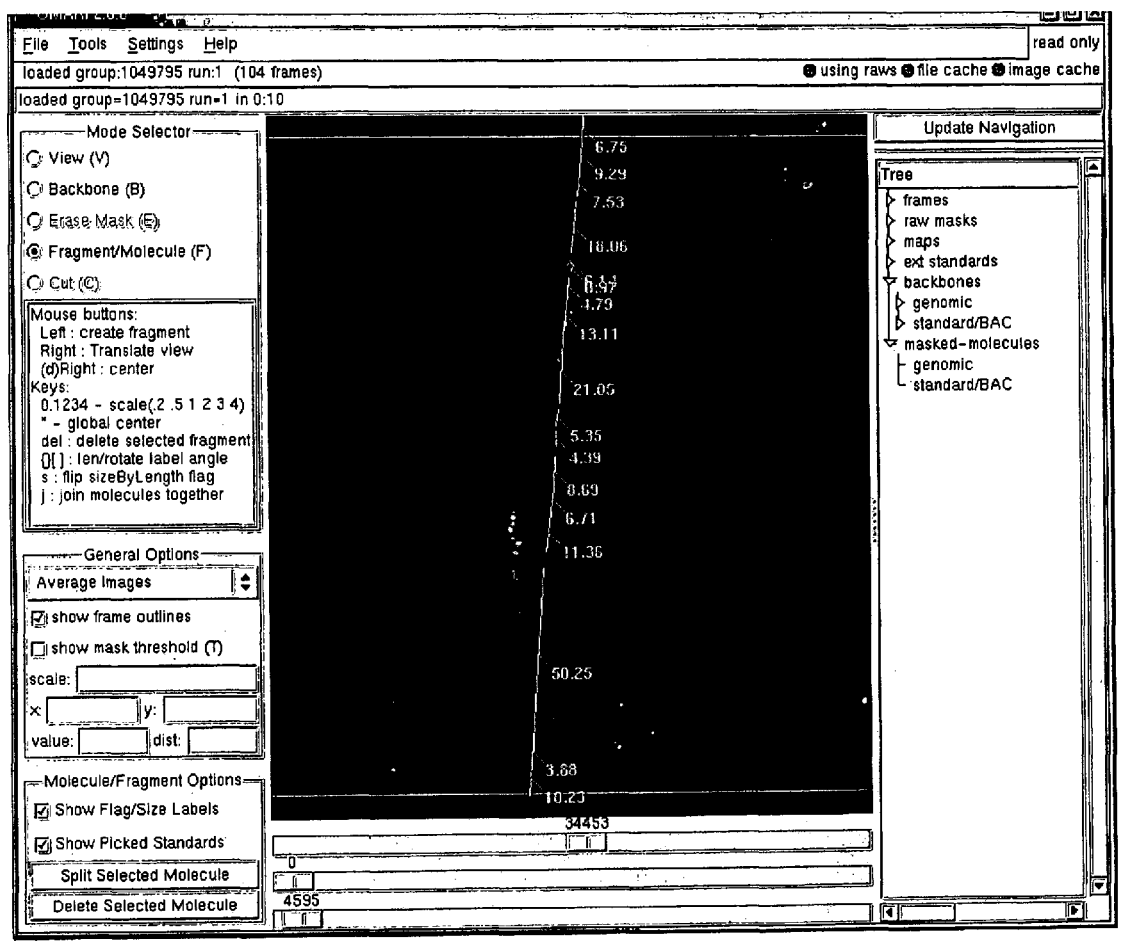
FIG. 3 is another screenshot of the user interface of the computer system for annotating single molecule images according to another embodiment of this disclosure, showing the mark up of a series of fragments of one single DNA molecule.

If there are no obvious cuts to add and no messy data to clean, the cut and erase modes of the annotation system may not be necessary for processing some groups of images. Fragment mode may be the only required feature; furthermore, the order of selecting fragments, adding cuts and erasing noise is not important, as long as fragments are grouped into appropriate molecules. Further, as shown in FIGS. 1, 2 and 3, the user interface of the computer annotation system in certain embodiments includes, on the left and below the mode selection radio buttons, a text panel and other fields which are useful in presenting additional information relating to the single molecules and fragments in view. When all marking has been achieved for a group, the user must save the file and export it for further processing.

Therefore, in the computer annotation system according to this disclosure, single molecules and fragments are represented in a manner that permits their visualization and mark up, either automatically in the system or by the user. An example of such representation is shown infra in Example 2, where an object is implemented as a C++ class which represents a single molecule having a set of fragments for mark-up in the computer annotation system in accordance with one embodiment of this disclosure.

The computer annotation system according to this disclosure enables simultaneous processing of a multitude of single molecule images. It allows integration of a great many images of single molecule fragments thereby creating a super-image of the fragments belonging to the same molecules. The system is highly robust and may handle a massive amount of image data without noticeable latency. That is, the images may be displayed and presented for mark up through the user interface in real time without perceivable delay by the user. Such robustness and fast response is enabled, in part, by an image caching system implemented in the computer annotation system in certain embodiments according to this disclosure.

For example, images are taken in overlapping patterns in optical mapping. An individual CCD image may capture 1316×1032 pixels which constitute 2.6 MB of data. A typical optical mapping surface has a potentially image-able area of approximately 20 mm×20 mm. This translates into a potential data image of 298,507×298,507 pixels, which may constitute an overlapping collage with 20% overlap/of 283×361-110, 653 images, i.e., 280 GB of data. Thus, theoretically, up to 280 GB of image data may need to be visualized at one time in the context of optical mapping of single molecules. In practice, collages from optical mapping channels may range from 100-300 images or 260 MB to 780 MB of data.

To process these large datasets, an image caching system is separately implemented in the computer annotation system in certain embodiments according to this disclosure, without resorting to the default, general purpose virtual memory caching built in the operating systems. Object oriented techniques may be used in implementing this image caching system. An exemplary procedure shown in Example 3 infra is implemented in C++ which renders colored mark up on single molecule fragments. The image processing in this procedure reflects optimized caching, e.g., overlap averaging and loading on demand of the image data. The load-on-demand approach works to maximize the efficiency of the system. For example, as the process initiates, the rectangle area information is read for each image such that a "global virtual data object" learns where each image is located. As program routines or procedures access this global data object, the images are loaded as needed. The global data object caches these images, and flushes them when the raw image cache is exceeded. An application program interface (API) is set up in the image caching system through which a collage of images appears as one large image that constitutes a large two-dimensional array of data. The data of such two-dimensional array can then be directly accessed by the computer annotation system. As such, an entire group of images may be processed by the computer annotation system as if it were a single image. Essentially, the system converts a massive number of images into one manageable super-image. The image of a group of single molecule fragments shown in FIG. 1 is an example of such a super-image constructed using the images collected from optical mapping of restriction enzyme digested genomic DNA molecules.

The image caching system in another embodiment of this disclosure may, in addition, reduce processor load for panning, zooming, and image adjustment. This is enabled by another layer of caching provided by the image caching system: a "tile" cache implemented by the display engine, i.e., through the user interface. The display or the image view in the user interface is broken into tiles of a fixed size with a set of display parameters, such as zoom factor, tinting, and location. As the user pans and zooms the images in the view, the display engine or the user interface creates new tiles as needed or grab the tile from a cache if it already exists. See, e.g., Example 3 infra. The high locality of reference in image data processing improves overall efficiency of the system. The tile creation is optimized in this embodiment to provide for desired responsiveness. Once the tiles are created, the user response becomes instantaneous. The implementation of the image caching system according to this embodiment may therefore permit image visualization in the computer annotation system with nearly infinite zoom and panning at a seamless response rate.

In various embodiments, the computer annotation system according to this disclosure may be implemented to work with full color, i.e., 16, 24 bit display, which offers high quality visibility. Various programming languages may be used to implement the computer annotation system, including, e.g., C, C++ used in Examples 1, 2 and 3 infra, and any other comparable language. In one embodiment, the GIMP toolkit (the GTK library,) is used to implement the graphic user interface; it provides desirable portability and allows the system to run on Linux, Sun Solaris and a variety of other operating systems.

The computer annotation system according to this disclosure may be implemented and deployed over a computer network in certain embodiments. The database to which the system connected and from which the system retrieves image data may be a distributed database over a network. In other embodiments, additional connectors may be included in the computer annotation system which link to additional databases. These additional databases may have stored therein single molecule image data, other single molecule data or other kinds of biomedical data. These various kinds of data may be retrieved by the system upon the request of the user and used to aid as well as validate the markings and annotations of single molecules.

Thus, the computer annotation system in various embodiments according to this disclosure, through its user interface allows a user to identify and add markings or annotations to single molecules. The markings and annotations may also be input by the user or automatically generated by the system based on the information stored in the connected database. The molecules marked or annotated may subsequently be mapped onto a restriction map if desired.

Various embodiments of this disclosure are further described by the following examples, which are only illustrative of the embodiments but do not limit the underlining invention(s) in this disclosure in any manner.

It is to be understood that the description, specific examples and data, while indicating exemplary embodiments, are given by way of illustration and are not intended to limit the present invention(s) in this disclosure. All references cited herein for any reason, are specifically and entirely incorporated by reference. Various changes and modifications which will become apparent to a skilled artisan from this disclosure are considered part of the invention(s) of this disclosure.

As used herein and in the following claims, articles such as "a," "an," "the" and the like can mean one or more than one, and are not intended in any way to limit the terms that follow to their singular form, unless expressly noted otherwise. Unless otherwise indicated, any claim which contains the word "or" to indicate alternatives shall be satisfied if one, more than one, or all of the alternatives denoted by the word "or" are present in an embodiment which otherwise meets the limitations of such claim.

The invention claimed is:

1. A computer system communicatively linked to a database storing single molecule image data and corresponding identifying data, the computer system programmed to:
    selectively retrieve at least two single molecule image data from the database wherein each single molecule image data depicts a region of a restriction fragment and comprises at least one pixel having image and intensity level data, and wherein the single molecule image data each include at least one pixel representing an overlapping region of the same single molecule image;
    calculate an average intensity level for at least one of the single molecule image data retrieved from the database by averaging an intensity level of each pixel of the at least one single molecule image data;
    display the at least two single molecule image data retrieved from the database on a user interface;
    display the intensity level for each pixel of the at least two single molecule image data retrieved from the database on the user interface;
    differentiate at least one restriction fragment in the single molecule image data from a background in the single molecule image data by applying an intensity level threshold analysis to each pixel of the single molecule image data;
    magnify each of the at least one restriction fragments for display on the user interface;
    form a collage by aligning the overlapping regions of the at least two single molecule image data;
    generate a linear representation of the restriction fragments by:
        (a) receiving an input signal from a marking tool provided to a user, the input signal indicating a point on the user interface associated with a pixel of the single molecule image data;
        (b) repeating step (a) to define successive points in a single restriction fragment;
        (c) retrieving the single molecule image data associated with points between each successive point; and
        (d) storing the retrieved single molecule image data as the single restriction fragment;
    associate the restriction fragments;
    order the associated restriction fragments based on their relative positions; and
    store the ordered restriction fragments as a restriction map in a file adapted for use in map generation.

2. The computer system of claim 1, further programmed to visually distinguish the at least two restriction fragments displayed on the user interface.

3. The computer system of claim 1, wherein the database is an object database.

4. The computer system of claim 1, wherein the single molecule image data is derived from optical signals derived from atomic force microscopy.

5. The computer system of claim 1, wherein the restriction fragment is displayed on the user interface as a generally contiguous region of the single molecule image data having an intensity level greater than the intensity level threshold.

6. The computer system of claim 1, further programmed to display a backbone mark-up on the user interface, wherein the backbone mark-up is a graphic overlay comprising lines connecting the successive points.

7. The computer system of claim 6, further programmed to receive an input signal from a marking tool provided to a user indicating a selected restriction fragment to remove from the list of selected restriction fragments.

8. The computer system of claim 1, further programmed to:
receive an input signal from a marking tool provided to a user, the input signal indicating a point within a restriction fragment displayed on the user interface;
select the restriction fragment;
highlight the selected restriction fragment on the user interface;
add the selected restriction fragment to a list of restriction fragments; and store the selected restriction fragment in a file adapted for use in map generation.

9. The computer system of claim 1, further programmed to receive an input signal from a marking tool provided to a user, the input signal indicating a point of the restriction fragment to add a cut; and
divide the restriction fragment into a first restriction fragment and a second restriction fragment; wherein the first restriction fragment ends at the cut and the second restriction fragment starts at the cut.

10. The computer system of claim 1, further programmed to display graphic overlays on the molecule fragments on the user interface; wherein the graphic overlays contain corresponding identifying data.

11. A computer-implemented method for selecting single restriction fragments from single molecule image data, wherein the single molecule image data comprises pixels having image and intensity data, the computer-implemented method comprising the steps of:

obtaining the single molecule image data from a database; wherein the single molecule data depicts a region of a restriction fragment and comprises at least one pixel;
calculating an intensity level for each pixel of the single molecule image data;
calculating an average threshold intensity of the single molecule image data;
displaying a portion of the single molecule image data using a user interface;
marking each pixel of the single molecule image data having a threshold intensity level greater than the average threshold intensity as a pixel of a restriction fragment image on the user interface;
receiving an input signal from a marking tool provided to a user via the user interface, the input signal identifying one or more pixels of the single molecule image data;
scaling a magnification of the restriction fragment for display on the user interface;
forming a single restriction fragment from a plurality of contiguous pixels of the single molecule image data, the plurality of contiguous pixels of the restriction fragment image including a pixel identified by the user input;
displaying the restriction fragment via the user interface; and
storing the restriction fragment in the database in a form adapted for use in map generation.

12. The method of claim 11, wherein the step of marking further comprises receiving at least two coordinates of pixels in the single molecule image data and marking all of pixels in a generally linear direction between the coordinates as pixels of a restriction fragment image.

13. The method of claim 11, further comprising the step of joining two or more molecule fragment images into a single molecule image comprising the steps of:
generating linear representations of each restriction fragment image;
associating two or more restriction fragment images;
ordering the two or more restriction fragment images based on their relative positions; and
storing the ordered restriction fragment images as a restriction map.

* * * * *